(12) United States Patent
Schmieding et al.

(10) Patent No.: US 7,678,134 B2
(45) Date of Patent: Mar. 16, 2010

(54) KNOTLESS ANCHOR FOR TISSUE REPAIR

(75) Inventors: Reinhold Schmieding, Naples, FL (US); Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 771 days.

(21) Appl. No.: 10/839,295

(22) Filed: May 6, 2004

(65) Prior Publication Data
US 2005/0080455 A1  Apr. 14, 2005

Related U.S. Application Data

(60) Provisional application No. 60/509,940, filed on Oct. 10, 2003.

(51) Int. Cl.
*A61B 17/04* (2006.01)
*A61B 17/84* (2006.01)

(52) U.S. Cl. ........................................ 606/232; 606/300

(58) Field of Classification Search .................. 606/72, 606/73, 74, 75–77, 151, 219, 232, 103; 411/386, 411/387.5, 387.7, 387.8, 393, 403–406, 493, 411/495, 497, 499; 81/460; 279/103; 433/173, 433/174; 24/130
See application file for complete search history.

(56) References Cited

U.S. PATENT DOCUMENTS

| 2,046,837 | A | * | 7/1936 | Phillips ........................ 81/460 |
|---|---|---|---|---|
| 3,762,733 | A | * | 10/1973 | Lana ........................... 279/103 |
| 5,176,682 | A | * | 1/1993 | Chow ........................... 606/72 |
| 5,236,445 | A | | 8/1993 | Hayhurst et al. |
| 5,464,427 | A | * | 11/1995 | Curtis et al. ................. 606/232 |
| 5,480,403 | A | * | 1/1996 | Lee et al. ....................... 606/72 |
| 5,486,197 | A | * | 1/1996 | Le et al. ...................... 606/232 |
| 5,522,844 | A | | 6/1996 | Johnson |
| 5,980,558 | A | * | 11/1999 | Wiley ......................... 606/232 |
| 6,024,758 | A | | 2/2000 | Thal |
| 6,126,663 | A | * | 10/2000 | Hair ............................. 606/72 |
| 6,241,732 | B1 | * | 6/2001 | Overaker et al. .............. 606/72 |
| 6,517,542 | B1 | * | 2/2003 | Papay et al. ................. 606/232 |
| 6,517,564 | B1 | * | 2/2003 | Grafton et al. ................ 606/72 |
| 6,641,596 | B1 | * | 11/2003 | Lizardi ....................... 606/232 |
| 6,685,728 | B2 | * | 2/2004 | Sinnott et al. ............... 606/232 |
| 6,730,092 | B2 | * | 5/2004 | Songer ......................... 606/72 |
| 7,108,710 | B2 | * | 9/2006 | Anderson .................... 606/232 |
| 2002/0161401 | A1 | | 10/2002 | Steiner |

FOREIGN PATENT DOCUMENTS

| EP | 0 464 479 | 1/1992 |
|---|---|---|
| EP | 1 199 035 | 4/2002 |
| WO | WO 01/06933 | 2/2001 |

\* cited by examiner

*Primary Examiner*—Julian W Woo
(74) *Attorney, Agent, or Firm*—Dickstein Shapiro LLP

(57) ABSTRACT

A knotless suture anchor for reattachment of tissue to bone features a barbed body having a Y-shaped slot formed distally for capturing a length of suture. The suture is passed through the tissue to be reattached, and a simple knot formed in the suture is captured in the slot on the suture anchor. The anchor is installed with the captured suture into a pre-formed pilot hole to draw the tissue to the bone.

12 Claims, 6 Drawing Sheets

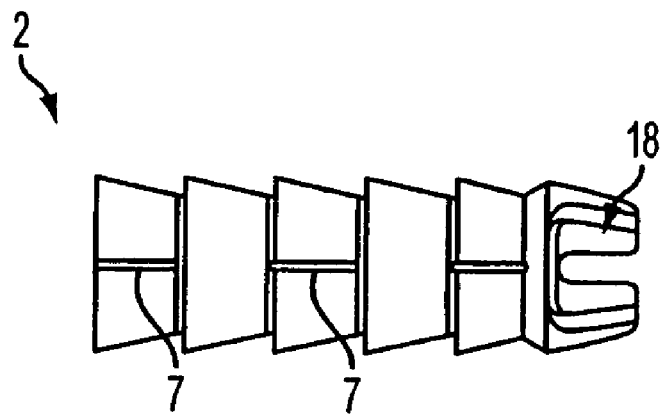
FIG. 3
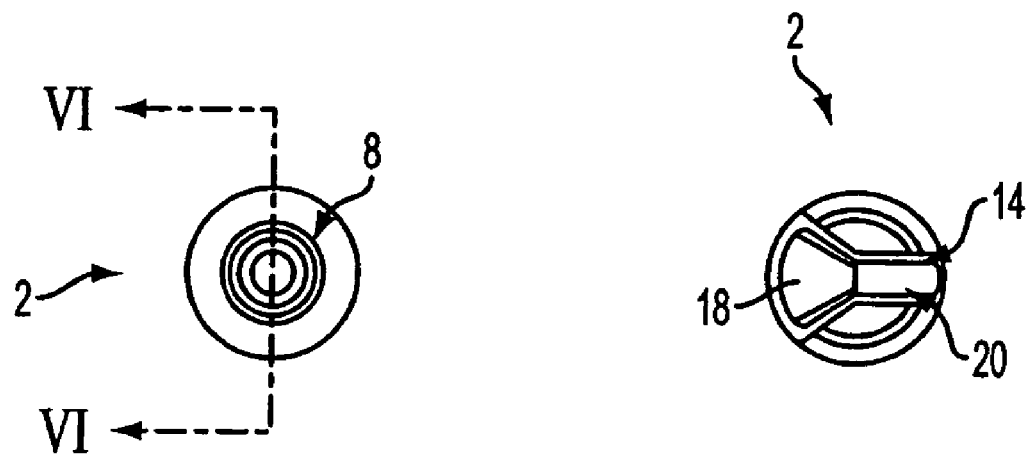
FIG. 4
FIG. 5

KNOTLESS ANCHOR FOR TISSUE REPAIR

This application claims the benefit of U.S. provisional Appl. No. 60/509,940 filed Oct. 10, 2003.

BACKGROUND OF THE INVENTION

1. Field of the Invention

The present invention relates to apparatus and methods for tissue repair, and more particularly to techniques using knotless suture anchors for reattaching soft tissue to bone.

2. Description of the Related Art

When soft tissues, such as tendons or ligaments, detach from bone, it is often necessary to reconnect the structures surgically. Techniques and devices that have been developed generally involve tying the soft tissue with suture attached to an anchor secured in a hole provided in the bone tissue. Reattachment with suture involves knot-tying, which can present difficulties in completing the knots and applying appropriate tension, especially when operating on small joints such as those in the hand and wrist. It would be beneficial to reattach tissue torn from bone using minimal knot tying.

BRIEF SUMMARY OF THE INVENTION

The present invention provides a small suture anchor having a barbed body. A slot formed on the distal end of the anchor captures a knotted length of suture. The slot has a V-shaped opening on one side which will capture a simple overhand knot formed in the suture. The suture is passed through the tissue to be reattached to bone, and the knot is formed about one anchor's length from the tissue. The anchor is driven with the captured suture into a pilot hole formed in the bone to draw the tissue with the suture to the bone.

BRIEF DESCRIPTION OF THE DRAWINGS

FIG. 3 is a plan view of the knotless suture anchor of FIGS. 1 and 2;

FIG. 4 is a top end view showing the proximal end of the knotless suture anchor of FIGS. 1-3;

FIG. 5 is a bottom view showing the distal end of the knotless suture anchor of FIGS. 1-4;

DETAILED DESCRIPTION OF THE INVENTION

Figure 1:
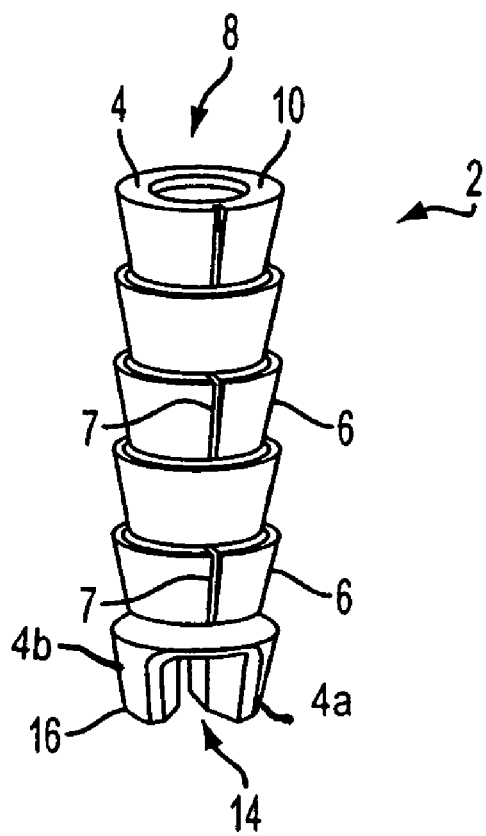
FIG. 1 is a perspective view of a knotless suture anchor according to the present invention.

Referring initially to FIGS. 1-7, a suture anchor 2 according to an exemplary embodiment of the present invention includes a generally cylindrical body 4 having a plurality of circumferential barbs 6. Barb breaks 7 are formed in each barb 6 on alternating sides of the anchor body 4. Suture anchor 2 is made of a bioabsorbable polymer or copolymer, preferably an absorbable polymer such as poly (L-lactide-co-D,L-lactide 70:30).

An opening 8 is formed in a proximal end 10 of suture anchor 2. Opening 8 provides access to a closed-ended cannulation 12 (FIG. 6) formed inside suture anchor body 4. Sidewalls of the cannulation 12 are smooth. Cannulation 12 narrows toward the closed, distal end and is shaped to accommodate a correspondingly shaped anchor driver described in detail below.

Figure 2:
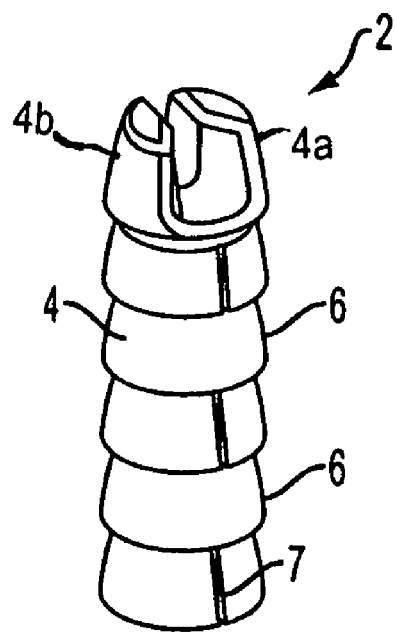
FIG. 2 is another perspective view of the knotless suture anchor of FIG. 1.
Figure 6:
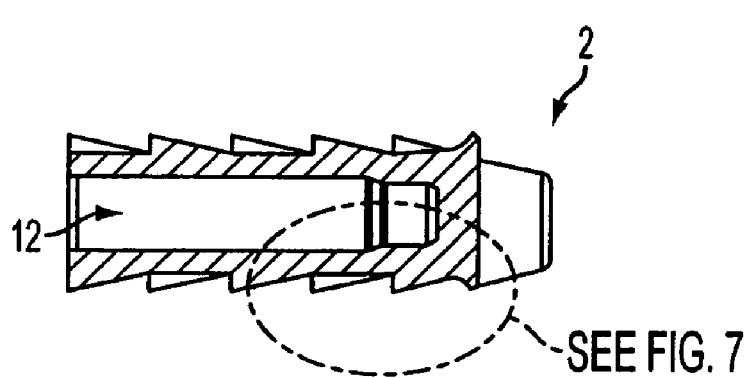
FIG. 6 is a sectional view of the knotless suture anchor of FIGS. 1-5 taken along the line VI-VI of FIG. 4.
Figure 7:
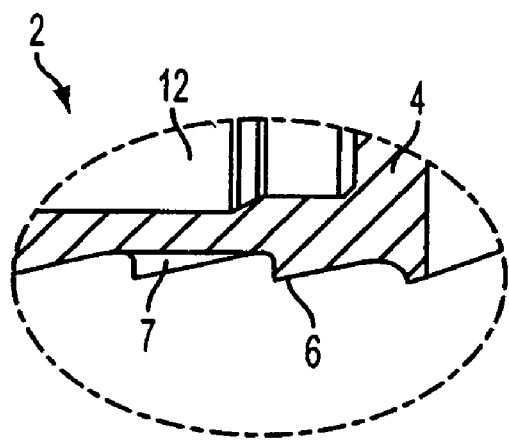
FIG. 7 is an enlarged detail of the knotless suture anchor of FIGS. 1-6 taken of section VII in FIG. 6.

A slot 14 is formed on a distal end 16 of suture anchor 2. As shown in FIGS. 1 and 2, for example, the slot 14 is defined by opposing members 4a, 4b of the body 4 of suture anchor 2 that extend about parallel to the longitudinal axis of the suture anchor 2. Viewed from the distal end, as shown in FIG. 5, the slot has a Y-shaped configuration defined by the opposing members 4a, 4b, such that the slot 14 exhibits a wide, tapering cleft 18 joined to a narrow channel 20. Accordingly, the tapered cleft 18 of the slot 14 accommodates and captures a knot formed in a length of suture. A straight portion of the knotted suture passed through the slot 14 slides into narrow channel 20, and a knot in the knotted suture is captured and confined in tapering cleft portion 18 of slot 14.

Figure 8:
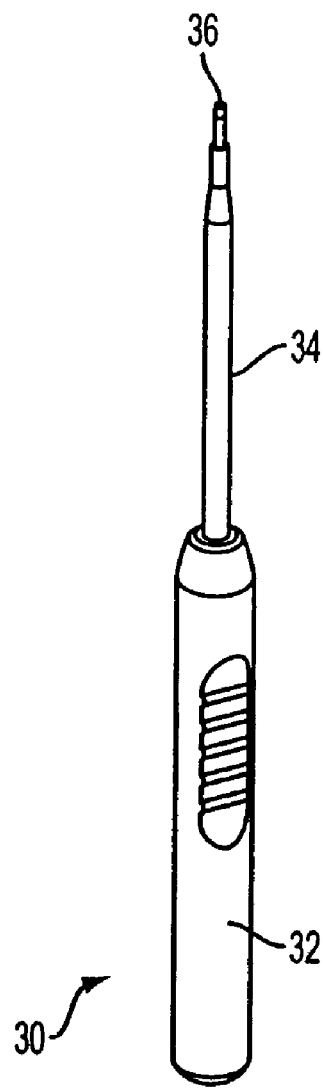
FIG. 8 is a perspective view of a driver for the suture anchor of FIGS. 1-7.
Figure 9:
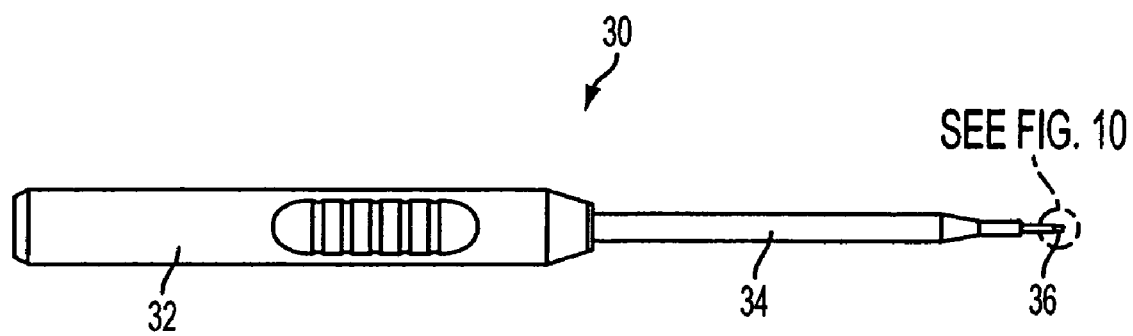
FIG. 9 is a plan view of the driver of FIG. 8.
Figure 10:
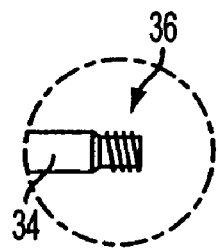
FIG. 10 is an enlarged plan view showing the distal end of the driver of FIGS. 8 and 9.

Referring to FIGS. 8-10, a driver 30 for suture anchor 2 according to an exemplary embodiment of the present invention includes a handle 32 secured to a shaft 34. Shaft 34 tapers distally to a threaded end 36 shown in detail in FIG. 10. Threaded end 36 fits securely into opening 12 for installation of anchor 2, as described below.

Figure 11:
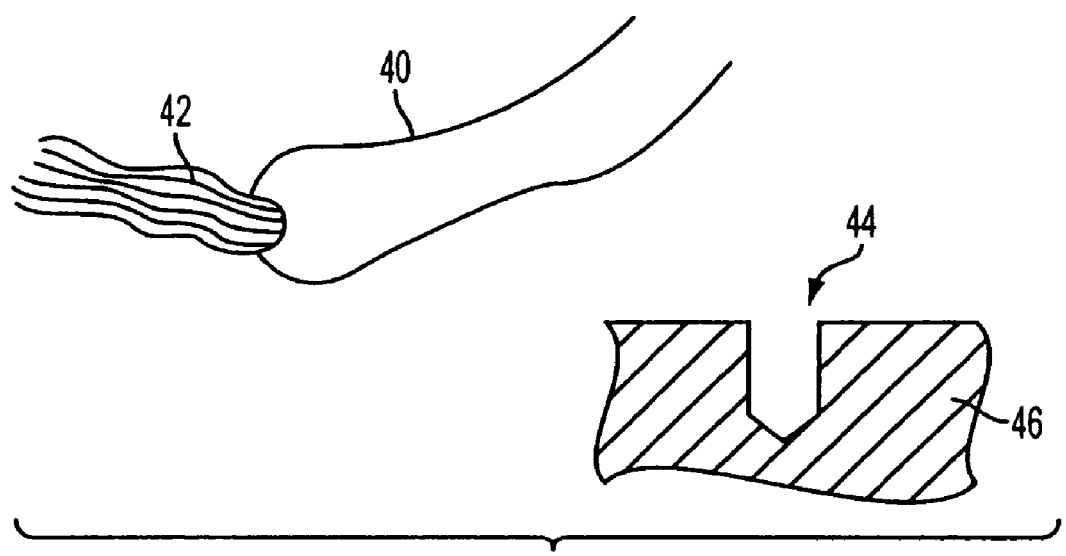
FIG. 11 is a schematic illustration of initial steps in a method of soft tissue repair according to the present invention.

Referring to FIGS. 11-14, an exemplary surgical method developed for scapho-lunate repair (wrist injury) is described. As shown in FIG. 11, a length of suture 40 (3-0 FiberWire®, available from Arthrex, Inc.) is passed through tissue 42 to be repaired. Separately, a pilot hole 44 is created in bone 46 at a desired location of tissue 42 reattachment.

Figure 12:
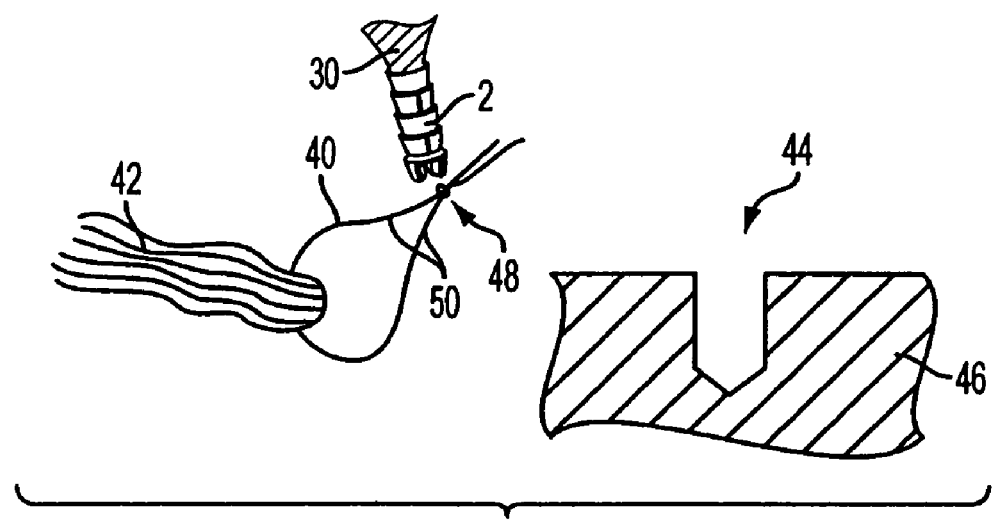
FIG. 12 is a schematic illustration of intermediate steps in the method for soft tissue repair initiated in FIG. 11.

Referring next to FIG. 12, a simple knot 48 is formed in the suture 40 (one surgeon's knot, one square knot, or a combination of one overhand and one underhand knot that includes both suture strands) at approximately one anchor length away from the tissue. The length of suture legs 50 between the tissue and the knot is established to provide appropriate fixation and tension for tissue 42 when the anchor is fully seated in pilot hole 44. Suture anchor 2 is secured to the threaded tip 36 of driver 30 and brought into proximity of suture 40 near knot 48.

Figure 13:
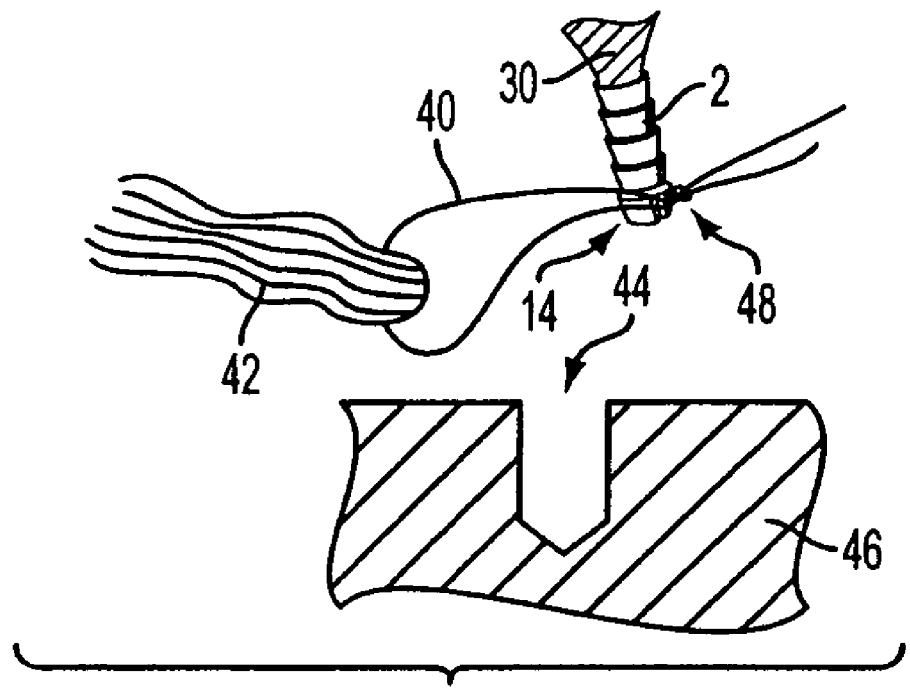
FIG. 13 is a schematic illustration of final steps in the method for soft tissue repair subsequent to steps illustrated in FIGS. 11 and 12.

Referring to FIG. 13, slot 14 at distal end 16 of anchor 2 is passed over suture 40 on legs 50 of the suture between tissue 42 and knot 48. The anchor 2 is oriented such that the narrow channel 20 of slot 14 is closest to tissue 42, and the tapering cleft portion 18 of slot 14 is closest to knot 48.

Figure 14:
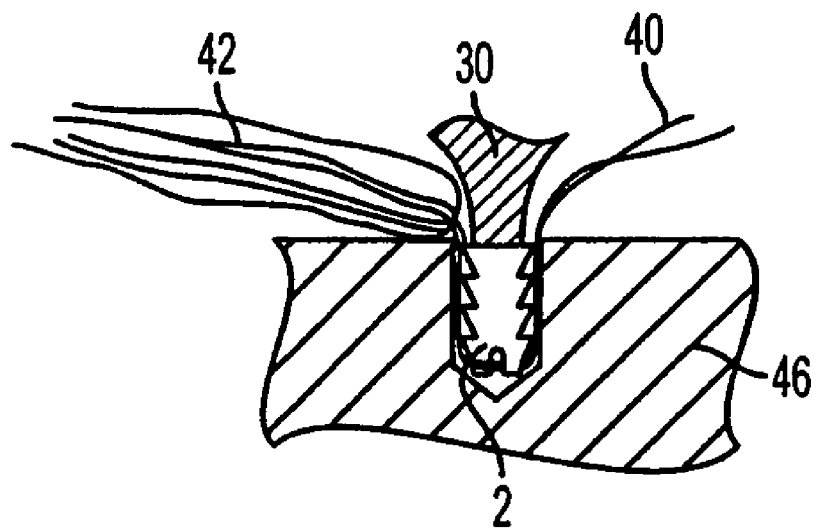
FIG. 14 is a schematic illustration of a repair resulting from the method of soft tissue repair illustrated in FIGS. 11-13.

Referring to FIG. 14, anchor 2 is inserted into pilot hole 44, drawing tissue 42 into the desired reattachment position when anchor 2 is fully inserted into pilot hole 44 using driver 30. Excess suture can be cut or used to tie down additional tissue.

Although the present invention has been described in connection with preferred embodiments, many modifications and variations will become apparent to those skilled in the art.

What is claimed is:

1. A suture anchor comprising:
a cylindrical body having a longitudinal axis, a proximal end and a distal end, wherein the cylindrical body is provided with a plurality of circumferential barbs and with a closed-ended cannulation provided inside of the cylindrical body, and wherein the distal end of the anchor is provided with two opposing members that extend about parallel to the longitudinal axis of the cylindrical body and define a slot for capturing a suture knot, and the proximal end of the suture anchor is configured to receive a driver, the slot having a Y-shaped configuration comprising a channel extending perpendicular to the longitudinal axis of the cylindrical body and a tapered cleft in communication with the channel, the tapered cleft being configured to capture and retain a suture knot therein.

2. A suture anchor according to claim 1, wherein the body is cylindrical.

3. A suture anchor according to claim 1, further comprising breaks formed in the circumferential barbs.

4. A suture anchor according to claim 3, wherein the breaks are formed alternately in the circumferential barbs.

5. A suture anchor according to claim 1 and made of a bioabsorbable material.

6. A suture anchor according to claim 5, wherein the bioabsorbable material is a polymer.

7. A suture anchor according to claim 6, wherein the polymer is a polylactide.

8. A suture anchor according to claim 1, wherein the closed-ended cannulation is open proximally.

9. A suture anchor according to claim 8, wherein sidewalls of the cannulation are smooth.

10. A suture anchor according to claim 9, wherein the cannulation narrows distally.

11. A suture anchor according to claim 8, wherein the cannulation is closed distally.

12. A suture anchor as recited in claim 1, wherein the proximal end of the suture anchor is provided with a smooth tapered cannulation designed to receive a tapered tip of the driver.

* * * * *